United States Patent
Varley et al.

(10) Patent No.: US 9,982,255 B2
(45) Date of Patent: May 29, 2018

(54) CAPTURE METHODOLOGIES FOR CIRCULATING CELL FREE DNA

(71) Applicant: Kailos Genetics, Inc., Huntsville, AL (US)

(72) Inventors: Katherine E. Varley, Madison, AL (US); D. Troy Moore, Huntsville, AL (US); Randall Bachmeyer, Huntsville, AL (US); David Kloske, Huntsville, AL (US)

(73) Assignee: Kailos Genetics, Inc., Huntsville, AL (US)

( * ) Notice: Subject to any disclaimer, the term of this patent is extended or adjusted under 35 U.S.C. 154(b) by 0 days. days.

(21) Appl. No.: 13/794,267

(22) Filed: Mar. 11, 2013

(65) Prior Publication Data

US 2014/0256558 A1 Sep. 11, 2014

(51) Int. Cl.
*C12Q 1/68* (2018.01)
*C12P 19/34* (2006.01)
*C12N 15/10* (2006.01)

(52) U.S. Cl.
CPC ....... *C12N 15/1068* (2013.01); *C12Q 1/6853* (2013.01)

(58) Field of Classification Search
CPC .............. C12N 15/1068; C12Q 1/6806; C12Q 1/6811; C12Q 1/6855
See application file for complete search history.

(56) References Cited

U.S. PATENT DOCUMENTS

| 9,315,857 | B2 * | 4/2016 | Fu ........................ C12Q 1/6837 |
| 2010/0129874 | A1 | 5/2010 | Mitra et al. |
| 2012/0077716 | A1 | 3/2012 | Godwin et al. |
| 2012/0301926 | A1 | 11/2012 | Chen et al. |

FOREIGN PATENT DOCUMENTS

WO 02/22872 A1 3/2002

OTHER PUBLICATIONS

International Search Report, International Patent Application No. PCT/US2014/020504, dated Jul. 22, 2014, 10 pages.
Zhang, K., et al., "Novel multiple PCR assay for characterization and concomitant subtyping of staphylococcal cassette chromosones mec types I to V in methicillin-resistant *Staphylococcus aureus*," J Clin Microbiol, Oct. 2005, Abstract only, vol. 43, No. 10.
Porreca, Gregory J., et al., "Multiplex amplification of large sets of human exons," Nature Methods, Nov. 2007, p. 931-936, vol. 4, No. 11.
Varley, Katherine Elena, et al., "Nested Patch PCR enables highly multiplexed mutation discovery in candidate genes," Cold Spring Harbor Laboratory Press, 2008, pp. 1844-1850, vol. 18.
Brown, John C., "What the Heck is PCR?", http://people.ku.eud/~jbrown/pcr.html, 1995, printed on Oct. 30, 2012, 3 pages.

* cited by examiner

*Primary Examiner* — Young J Kim
(74) *Attorney, Agent, or Firm* — Lewis Rice LLC (57) ABSTRACT

A nucleic acid patch method for amplifying target nucleic acid sequences in circulating free DNA or residual DNA samples where the defining ends of the target nucleic acid sequences are unknown.

2 Claims, 5 Drawing Sheets

CAPTURE METHODOLOGIES FOR CIRCULATING CELL FREE DNA

BACKGROUND

1. Field of the Invention

This disclosure is related to the field of devices, methods, systems and processes for capturing and amplifying targeted regions on circulating cell free DNA fragments. Specifically, for capturing and amplifying targeted regions on genomic DNA where the end points of the desired target are unknown or a portion of the end points of the desired target are known but it is unknown how much of the end point is present.

2. Description of Related Art

The completion of the decoding of the canonical genome sequences of all major model organisms, as well as the human species, has thrown open the door to elucidating the candidate genes associated with various human diseases. The application of the genetic origins of human disease can be very powerful to the understanding and development of treatments for these diseases. Examples of successful application of the genetic basis of disease in the clinic and clinical research settings includes the sequencing of candidate disease loci in targeted populations, such as the Ashkenazi Jews (Weinstein 2007), the sequencing of variants in drug metabolism genes to adjust dosage (Marsh and McLeod 2006), and the identification of genetic defects in cancer that make tumors more responsive to certain types of treatments (Marsh and McLeod 2006). Accordingly, medical re-sequencing of candidate genes in individual samples is becoming increasingly important in clinical settings and in clinical research. Medical re-sequencing requires the amplification and sequencing of many candidate genes in many patient samples. However, the ability to fully embrace the promise of the clinical-application of genetic-based research necessitates the development of new technology to lower the cost and increase the throughput of medical re-sequencing to make clinical applications more feasible.

As noted in United States Patent Application Publication No.: 2010/0129874, the entirety of which is specifically incorporated herein by reference to the extent not inconsistent with the disclosures of this patent, many of the current methods for analyzing sequence variation in a subset of the human genome generally rely on polymerase chain reaction ("PCR") to amplify targeted sequences (Greenman, et al. 2007; Sjoblom, et al., 2006; Wood, et al., 2007). However, efforts to multiplex PCR (i.e., target many regions across multiple samples in a single process) have been hampered by a dramatic increase in mispriming events as more primer pairs are used (Fan, et al. 2006). Further, the larger number of primer pairs utilized in multiplex PCR often results in inter-primer interactions that prevent amplification (Han, et al.). Therefore, separate PCRs for each region of interest generally must be performed. (Greenman, et al., 2007; Sjoblom, et al., 2006; Wood, et al., 2007). This creates a costly approach when hundreds of individual PCRs must be performed for each sample. Further, these methods often have inherent problems with multiplicity (i.e., the number of independent capture reactions which can be performed simultaneously in a single reaction), specificity (i.e., measured as the fraction of captured nucleic acids that derive from targeted regions), and uniformity (i.e., relative abundance of targeted sequences after selective capture). Ideally, a multiplex PCR model would perform each of these performance parameters (multiplicity, specificity and uniformity) well. As noted in United States Patent Application Publication No.: 2010/0129874, this was not accomplished by the currently utilized systems. Another problem was that currently utilized multiplex PCR methods and systems required a large amount of starting DNA to supply enough template for all of the required individual PCR reactions. This was a problem since DNA can serve as a limiting factor when working with clinical samples.

Because of these problems, there was a need in the art for a multiplexed PCR method that simultaneously amplified many targeted regions from a small amount of nucleic acid. United States Patent Application Publication No.: 2010/0129874 disclosed a method for amplifying at least two different nucleic acid sequences utilizing a multiplexed nucleic acid patch PCR which, in part, responded to this need in the art.

In general, the method disclosed in United States Patent Application Publication No.: 2010/0129874 relies on two rounds of target-specific enrichment, with discrete clean-up steps between each round, to confer more specific targeting and amplification than the previously known PCR systems and methodologies. Specifically, the disclosed methods require four oligonucleotide hybridizations per locus, resulting in more specific amplification than standard multiplex PCR, which requires only two hybridizations per locus.

In the first round, targeting primer pairs are designed for each target region (i.e., specific regions of interest within genomic DNA), and a low number of PCR cycles are performed. This low cycle amplification serves two functions: 1) it defines the target regions; and 2) it differentiates the target regions from non-targeted background DNA. The primers utilized in this round are designed to include uracil instead of thiamine, and are cleaved and removed by enzymes following the initial amplification. At the end of the first round, the ends of the target region are now internal to the PCR primer sequences.

In the second round, a target-specific enrichment, "patch oligonucleotides," are employed. The patch oligonucleotides are comprised of a string of oligonucleotides of variable length that contain, at a minimum, a sequence that is the reverse compliment to at least a portion of a sequence that defines the targeted region. Stated differently, each patch oligonucleotide is designed specifically for the ends of each target region, slowing ligation of universal adapters, and a protecting group. The patch oligonucleotides are annealed to the targeted regions and serve as a patch between targeted amplicons and universal primers. This targeting step delivers a higher level of specificity as only targeted regions can anneal with patch oligonucleotides. The universal primers, which anneal to the universal region of the patch oligonucleotides, then ligate to each target amplicon. This reaction is highly specific because thermostable ligases are sensitive to mismatched bases near the ligation junction (Barany 1991). An added level of selectivity is gained by degrading mispriming products as well as the genomic DNA with exonuclease. The selected amplicons are protected from degradation by a 3' modification on the universal primer. This hybridization and ligation of patch oligonucleotides to primer-depleted amplicons is followed by multi-template PCR amplification with primers corresponding to the universal sequences.

In the second round, the patch oligonucleotides confer additional and very high specificity in targeting regions of interest because the ligation is dependent on sequences immediately internal to the original primers used in the initial low cycle PCR. Thus, a further level of specificity is achieved by degrading any misprimed product and genomic DNA. Stated differently, enzymatic digestion is utilized to remove all non-protected DNA including any misprimed segment from the initial limited cycle step. The cleanup ensures that only the targeted regions are loaded onto the next generation sequencer for universal amplification—all off-target amplicons are degraded. Thus, in this process, all of the targeted regions are amplified and enriched simultaneously, in one tube, start to finish.

In sum, the methods disclosed in United States Patent Application Publication No.: 2010/0129874 addressed the need in the art for a multiplexed PCR method with the ability to amplify many targeted regions from a small amount of nucleic acid, allowing for the targeting of many regions across multiple samples, thereby providing an effective solution to maximize throughput capacity of sequencers.

While an advance in the art, the methods disclosed in United States Patent Application Publication No.: 2010/0129874 are still limited. Because these methods are based on defining the ends of nucleic acid sequences, they are generally not applicable in situations where the targeted region is located in fragmented DNA, residual DNA or circulating cell free DNA (circulating cell free DNA is produced through the process of cellular apoptosis and released into circulation). Stated differently, the methods disclosed in United States Patent Application Publication No.: 2010/0129874 are only applicable if the end of at least two nucleic acid sequences to which patches can be annealed are known. Thus, these methods are not applicable to capturing DNA fragments and circulating cell free DNA—i.e., situations in which the defining ends of the nucleic acid target sequences are unknown. Amongst other applications, capturing DNA fragments and circulating cell free DNA is important to the identification of genetic defects in fetal DNA circulating in maternal blood for the diagnosis of prenatal health issues. See Lo Y M, et al., "Presence of fetal DNA in maternal plasma and serum," *Lancet*, 350 (9076):485-7 (Aug. 16, 1997); Palomaki G E, et al., "DNA Sequencing of Maternal Plasma to Detect Down syndrome: An International Clinical Validation," *Genet Med*, Vol 13: No 11 (November 2011).

SUMMARY

Because of these and other problems in the art, described herein, among other things, is a nucleic acid patch method for amplifying target nucleic acid sequences in circulating free DNA or residual DNA samples where the defining ends of the target nucleic acid sequences are unknown.

In an embodiment, there is described a method for the capture and amplification of a targeted region of fragmented DNA (fgDNA), the method comprising: choosing one or more targeted regions of fgDNA for amplification; adding oligonucleotide patches to the fgDNA, the oligonucleotide patches binding to the ends of the one or more targeted regions creating double stranded DNA at the bound ends of the one or more targeted regions; adding enzymes to the fgDNA, the enzymes cleaving to the single-stranded DNA, resulting in a product with blunted double stranded DNA defined by the oligonucleotide patches bound to one or more reduced targeted regions; performing polymerase chain reaction; and sequencing the polymerase chain reaction amplicons of the one or more targeted regions.

In an embodiment of the method, the oligonucleotide patches contain one or more nucleotide terminal sequences.

In an embodiment of the method, the nucleotide terminal sequences comprise an adenine and a universal primer sequence.

In an embodiment of the method, the oligonucleotide patches are comprised of universal primers, protecting groups and nucleotide terminal sequences.

In an embodiment of the method, a multiplicity of oligonucleotide patch pairs are added to the reaction concurrently.

There is also described herein, a method for the capture and amplification of a targeted region of fragmented DNA, the method comprising: choosing one or more minimal targeted regions of fgDNA for capture and amplification; adding oligonucleotide patches to the fgDNA, the oligonucleotide patches comprising a universal primer sequence, protecting groups on at least on end, and a string of oligonucleotides of variable length, the string containing a sequence that is the reverse compliment to an end sequence that defines the one or more minimal targeted regions of fgDNA; binding the reverse nucleotide portion of the oligonucleotide patches to a portion of the one or more minimal targeted regions; filling in a remaining single-stranded region between the universal primer sequences and the oligonucleotide patches with polymerase; using ligation to join the universal primer sequences and the fgDNA into a single molecule; removing all unprotected primers and non-targeted DNA with enzymes; performing polymerase chain reaction; and sequencing the products of the polymerase chain reaction.

In an embodiment of the method, a multiplicity of oligonucleotide patches are added concurrently.

DESCRIPTION OF THE PREFERRED EMBODIMENT(S)

By way of background, polymerase chain reaction ("PCR") amplifies specific nucleic acid sequences through a series of manipulations including denaturation, annealing of oligonucleotide primer pairs and extension of the primers with DNA polymerase. These steps can be sequentially repeated, resulting in an exponential amplification of the number of copies of the original target sequence. Multiplex PCR is a variation of PCR that enables the simultaneous amplification of many targets of interest in one reaction by using more than one pair of primers. As noted previously, current multiplex PCR methods are hampered by the amplification of mispriming events, inter-primer interactions that prevent amplification as more primer pairs are used and cost.

Disclosed herein are various methods, processes and systems for the amplification of targeted sequences in fragmented genomic DNA where the ends abutting the targeted genomic sequences are unknown. In general, a targeted region is a user defined region to be captured for sequencing large portions of genomic DNA. It is often unknown what exact sequence is joining the two regions that are linked together.

Figure 1:
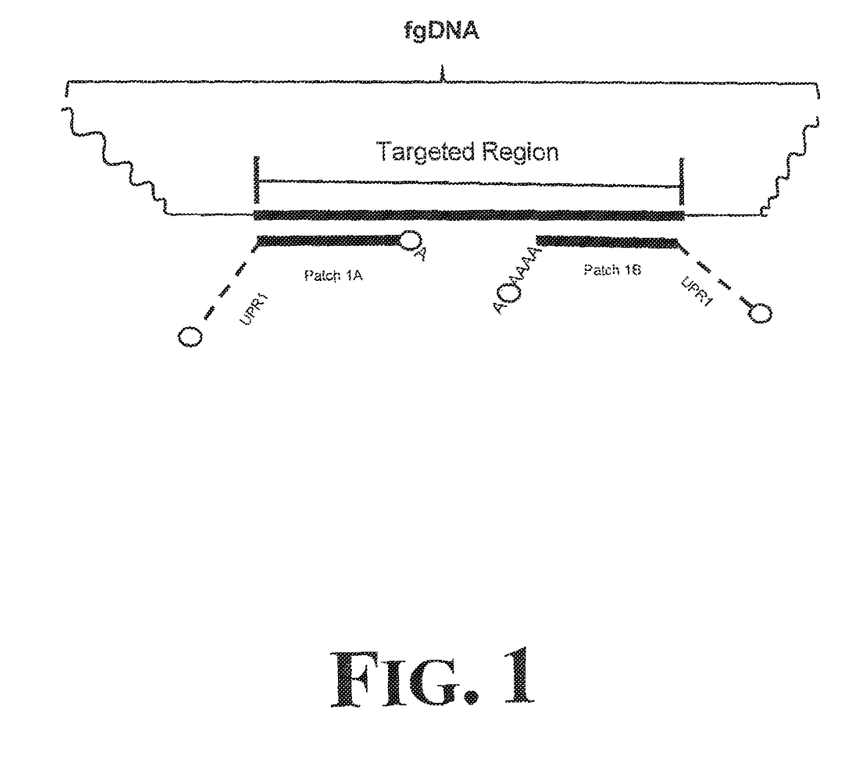
FIG. 1 depicts a step of an embodiment of the patch digest protection process in which the nucleic acid sequence of the oligonucleotide patches binds to targeted region(s) of fragmented DNA to create double stranded DNA at the bound ends of the targeted region(s).

In one embodiment, the method, process and system for the capture and amplification of a targeted region of fragmented DNA is patch digest protection (PDP). In general, in PDP one or more targeted regions of fgDNA (i.e., genomic DNA (gDNA) fragmented into a distribution of sizes) are chosen for capture and amplification by the PDP process. In a first step of PDP, oligonucleotide patches are added to the fgDNA. Oligonucleotide patches are a string of oligonucleotides of variable length that contain, at a minimum, a sequence that is the reverse compliment to an end sequence that defines the targeted region of fgDNA. It is contemplated that the oligonucleotide patches disclosed herein will also contain one or more nucleotide terminal sequences, preferably an adenine and a universal primer sequence, and protecting groups on one or both ends. Among other functions, the terminal sequences prevent the polymerase extension of the patch oligonucleotides. These oligonucleotide patches will be discussed more fully later in this application. In certain embodiments, it is contemplated that a multiplicity of oligonucleotide patch pairs (A/B) are added to the reaction concurrently. Once introduced, the oligonucleotide patches bind to the ends of the targeted region(s), protecting groups on one or both ends. This is depicted in FIG. 1 where patch 1A and patch 1B bind to the ends of the targeted region. This binding of the nucleic acid sequence of the patches to the targeted region creates a double stranded DNA at the bound ends of the targeted region, as depicted in FIG. 1.

Figure 2:
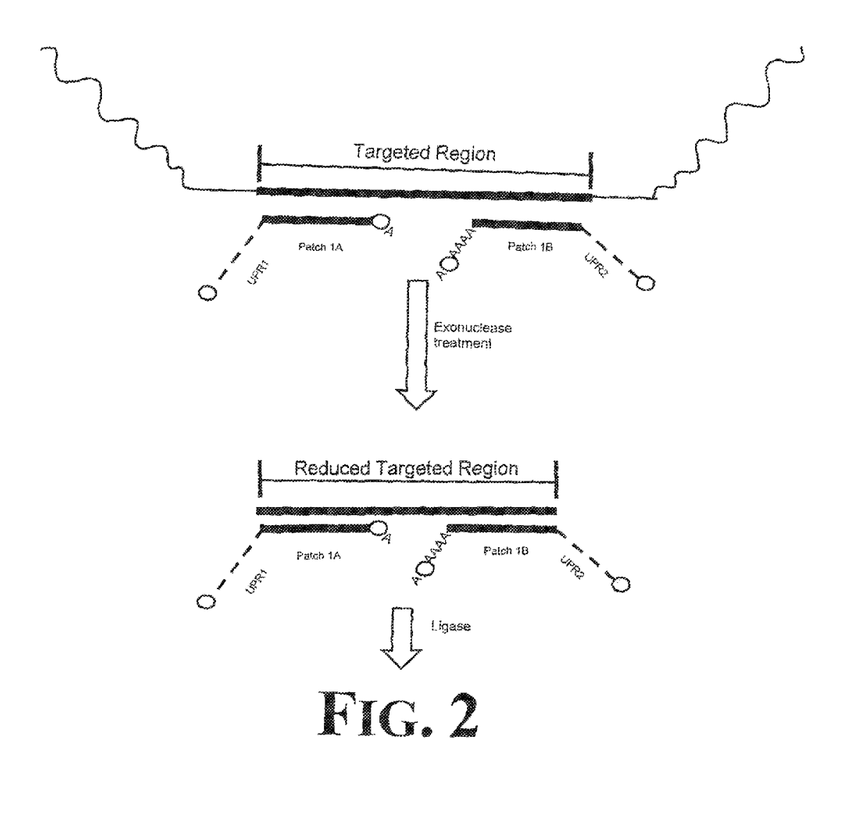
FIG. 2 depicts a step of an embodiment of the patch digestion process in which enzymes are utilized to cleave to the single-stranded DNA on the outer flanks of the oligonucleotide patches, resulting in a product with blunted double-stranded DNA ends defined by patches.

In a second step of the PDP process, following binding of the oligonucleotide patches to the ends of the targeted region, enzymes are utilized to cleave to the single-stranded DNA on the outer flanks of the oligonucleotide patches. These enzymes will be discussed more fully later in this application. This second step, which is depicted in FIG. 2, results in a product with blunted double stranded DNA ends defined by the patches (patches 1A and 1B in the depicted Figure) are bound to a reduced targeted region. The reduced target regions are protected from degradation in this step because they are flanked by double-stranded DNA. In general, as the term is used herein, a reduced targeted region is the subsection of fgDNA equal to or larger than a targeted regions, whose ends are defined by patches.

Figure 3:
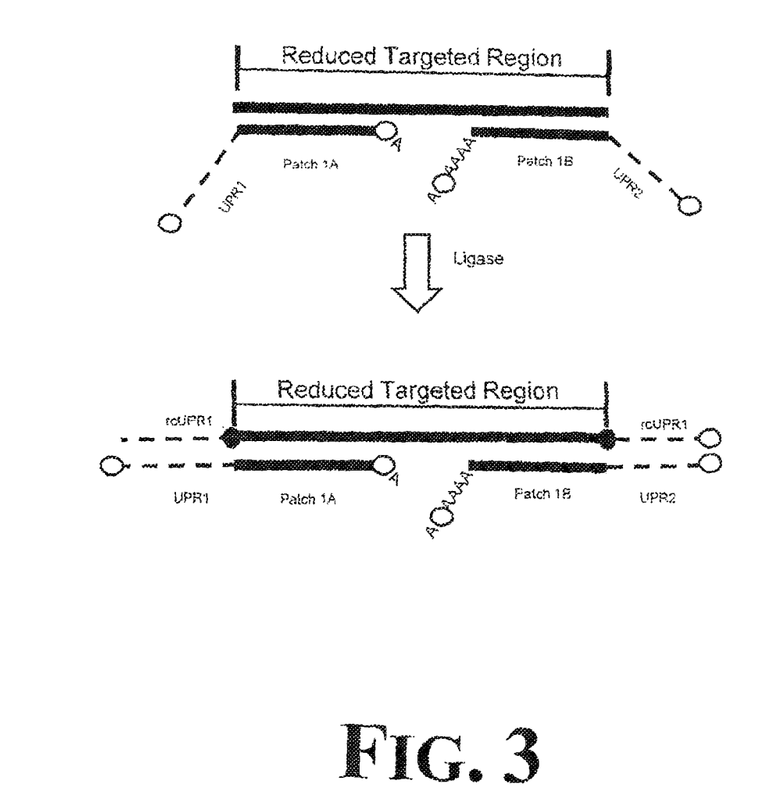
FIG. 3 depicts a step of an embodiment of the patch digestion process in which the oligonucleotide patches bound to the targeted regions serve as a connector to allow the ligation of the universal primers containing protecting groups to the end of the reduced targeted region.
Figure 4:
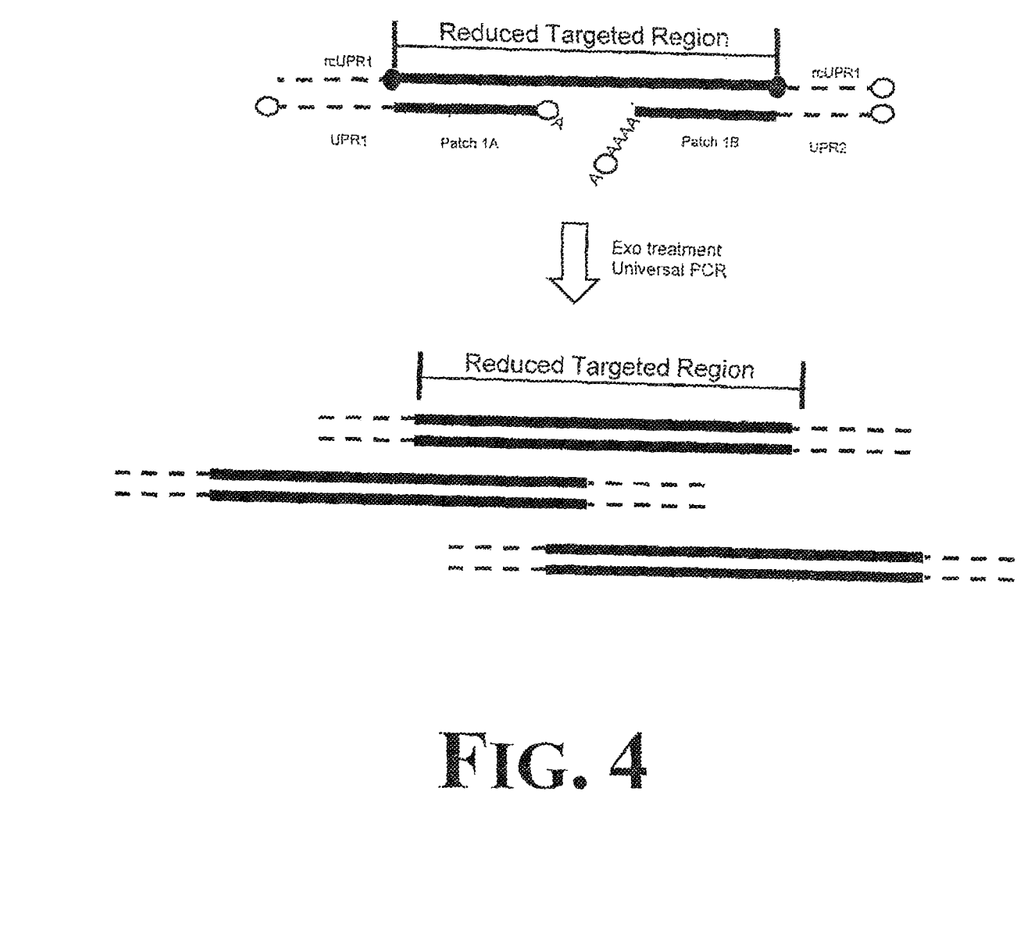
FIG. 4 depicts a step of an embodiment of the patch digestion process in which polymerase chain reaction is performed using universal primers to simultaneously amplify multiple targeted regions in the same reaction.

As noted previously, the oligonucleotide patches are comprised of universal primers, in addition to protecting groups and a nucleic acid sequence that will bind to a targeted region. Through these universal primers, the patches, in addition to binding to the target region thereby isolating the targeted region, serve as a connector to allow the ligation of the universal primers containing protecting groups to the end of the reduced targeted region. This process is depicted in FIG. 3. In a final step, as depicted in FIG. 4, PCR is performed using universal primers to simultaneously amplify multiple targeted regions in the same reaction. After amplification, the PCR product amplicons of the targeted regions can be sequenced.

In another embodiment, the method, process and system for the capture and amplification of a targeted region of fragmented DNA is patch the gap (PtG). In one contemplated scenario, patch the gap is utilized when it is known what the end of the targeted region is, but it is unknown how much is there. In PtG, one or more minimal targeted regions of fgDNA are chosen for capture and amplification by the PtG process. As the term is used herein, minimal targeted regions are fgDNA segments that contain a targeted region with ends that cannot be precisely defined by patches. In a first step of PtG, oligonucleotide patches are added to the fgDNA. The oligonucleotide patches utilized in PtG are comprised of a string of oligonucleotides of variable length that contain, at a minimum, a sequence that is the reverse compliment to an end sequence that defines the targeted region of fgDNA. Further, it is contemplated that the oligonucleotide patches disclosed herein for use in fgDNA also contain a universal primer sequence (UPR) and protecting groups on one or both ends. These oligonucleotide patches will be discussed more fully later in this application. In certain embodiments, it is contemplated that a multiplicity of patch pairs (A/B) are added to the reaction concurrently. Once added to the fgDNA, the reverse nucleotide portion of the patches anneal (or bind) to a portion of the minimal targeted region of the fgDNA, the universal primer sequences and the universal primer, as depicted in FIG. 5.

Figure 5:
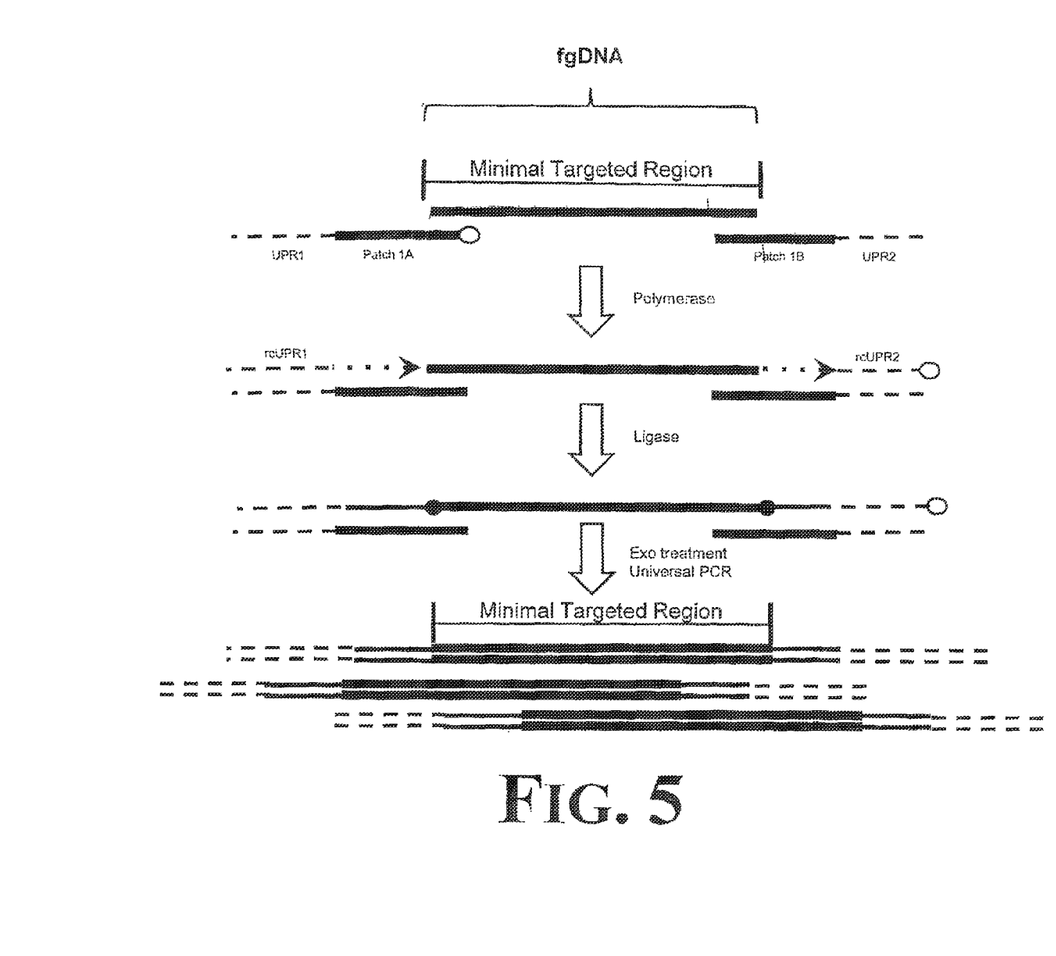
FIG. 5 depicts an embodiment of the patch the gap process.

In a next step, the remaining single-stranded region between the UPR and the patches is filled in by polymerase as depicted in FIG. 5. As depicted, the polymerase extension on the 5' end of the fgDNA is initiated from the universal primer and polymerizes double-stranded DNA until it reaches the fgDNA. Conversely, the polymerase extension on the 3' end is initiated from the fgDNA and polymerizes double stranded DNA until it reaches the end of the universal primer. Generally, a polymerase that lacks both strand displacement and 5'-3' exonuclease activity is utilized so that processivity of the polymerase is stopped when it reaches double-stranded DNA.

In a third step in PtG, ligation is used to join the universal primers and fgDNA into a single molecule. As noted previously, the universal primers generally contain protecting groups. In a next step, enzymes are used to remove all of the unprotected primers and non-targeted DNA. In a final step, PCR is performed using universal primers to simultaneously amplify many targeted regions in the same reaction. Subsequent to this amplification, the PCR products can be sequenced.

In order to better understand these systems, methods and processes of PDP and PtG disclosed herein, the following terms, components and conditions of the described processes and methods are further defined.

A) Nucleic Acid Template

The methods, systems and processes disclosed herein may be used to amplify nucleic acid sequences. Generally, nucleic acid sequences are found in a nucleic acid template. It should be understood that the nucleic acid template described herein may be from any sample that contains nucleic acid molecules. The nucleic acid template may be from humans, animals, plants, microorganisms, or viruses. The sample may be fresh, from archeological or forensic samples, or from preserved samples such as paraffin-embedded tissue. The sample may be a solid tissue or a physiological fluid such as blood, serum, plasma, saliva, ocular lens fluid, cerebral spinal fluid, sweat, urine, milk, ascites fluid, lymphatic fluid, mucous, synovial fluid, peritoneal fluid, sputum fluid or amniotic fluid. Nucleic acid templates may be prepared from the sample methods well known to those of ordinary skill in the art. Alternatively, the sample containing the nucleic acid template may be used directly.

The nucleic acid template may be DNA, RNA, or a complementary DNA (cDNA) sequence that is synthesized from a mature messenger RNA. If the nucleic acid template is RNA, the RNA may be reverse transcribed to DNA using methods well known to persons skilled in the art. In a preferred embodiment, the nucleic acid template is DNA.

In some embodiments, suitable quantities of nucleic acid template for the invention may be 10, 9, 8, 7, 6, 5, 4, 3, 2, 1, 0.5, 0.1, 0.05, 0.01, 0.005, 0.001 .mu.g or less. In preferred embodiments, suitable quantities of nucleic acid template for the invention may be 1000, 900, 675, 450, 225, 112, 70, 50, 20, 1.6 ng or less.

In some embodiments, the nucleic acid template may be treated to prepare the template for specific applications of the invention. In one embodiment, the nucleic acid template may be treated with bisulfite to determine the pattern of methylation. Nucleic acid templates may be treated with bisulfite using methods well known to those of skill in the art, and may be performed using commercially available reagents, following manufacturer's protocols, such as by using the EZ DNA Methylation-Gold Kit™ (Zymo Research), the Imprint™ DNA Modification Kit (Sigma), or the like.

Further, in certain preferred embodiments, the method and processes of amplification discussed herein are used to amplify nucleic acid sequences in circulating cell free DNA, DNA fragments and/or residual DNA. Examples of such circulating cell free DNA amplification applications include, but are not limited to, detecting genetic disorders in a fetus using blood samples from a pregnant woman; diagnosing and monitoring cancer patients for cancer type, stage, recurrence and/or drug resistance; discovery, detection, and monitoring of biomarkers in other disease states, such as cardiac disease, neurological disorders, or infectious disease; detecting genetic material from microbes and pathogens in environmental, medical or industrial samples; and determining the identity of an individual/organism from a residual sample, for example, a fingerprint of a suspect from a crime scene or a genetically modified corn strain in a GMO-free cereal (in both of these scenarios, there is only a small amount of DNA material).

B) Polymerase

In one embodiment, the nucleotide polymerase disclosed herein and utilized, for example, in the disclosed PtG process, may be a DNA polymerase. In another embodiment, the nucleotide polymerase may be a thermostable polymerase. A thermostable polymerase is an enzyme that is relatively stable to heat and eliminates the need to add enzyme prior to each PCR cycle. Non-limiting examples of thermostable polymerases may include polymerases isolated from the thermophilic bacteria *Thermus aquaticus* (Taq polymerase), *Thermus thermophilus* (Tth polymerase), *Thermococcus litoralis* (Tli or VENT™ polymerase), *Pyrococcus furiosus* (Pfu or DEEPVENT™ polymerase), *Pyrococcus woosii* (Pwo polymerase) and other *Pyrococcus* species, *Bacillus stearothermophilus* (Bst polymerase), *Sulfolobus acidocaldarius* (Sac polymerase), *Thermoplasma acidophilum* (Tac polymerase), *Thermus rubber* (Tru polymerase), *Thermus brockianus* (DYNAZYME™ polymerase) *Thermotoga neapolitana* (Tne polymerase), *Thermotoga maritime* (Tma) and other species of the *Thermotoga* genus (Tsp polymerase), and *Methanobacterium thermoautotrophicum* (Mth polymerase). The applicable methods and processes disclosed herein may contain more than one thermostable polymerase enzyme with complementary properties leading to more efficient amplification of target sequences. For example, a nucleotide polymerase with high processivity (the ability to copy large nucleotide segments) may be complemented with another nucleotide polymerase with proofreading capabilities (the ability to correct mistakes during elongation of target nucleic acid sequence), thus creating a PCR reaction that can copy a long target sequence with high fidelity. The thermostable polymerase may be used in its wild type form. Alternatively, the polymerase may be modified to contain a fragment of the enzyme or to contain a mutation that provides beneficial properties to facilitate the PCR reaction. In one embodiment, the thermostable polymerase may be Taq polymerase. Many variants of Taq polymerase with enhanced properties are known and include AmpliTaq™, AmpliTaq™ Stoffel fragment, SuperTaq™, SuperTaq™ plus, LA Taq™, LApro Taq™, and EX Taq™.

C) PCR Reaction Conditions

Buffer conditions for PCR reactions are known to those of ordinary skill in the art. PCR buffers may generally contain about 10-50 mM Tris-HCl pH 8.3, up to about 70 mM KCl, about 1.5 mM or higher MgCl.sub.2, to about 50-200 .mu.M each of dATP, dCTP, dGTP and dTTP, gelatin or BSA to about 100 .mu.g/ml, and/or non-ionic detergents such as Tween-20 or Nonidet P-40 or Triton X-100 at about 0.05-0.10% v/v. In some embodiments, betaine may be added to the PCR reactions at about 0.25 to about 1 M.

In some embodiments, the multiplex PCR reaction performed subsequent to PDP or PtG may contain 30, 40, 50, 60, 70, 80, 90, 100, 200, 300, 400, 500, 600, 700, 800, 900, 1000, 1100, 1200 or more primer pairs. Not all primer pairs will amplify targets with the same efficiency. In some embodiments, PCR primer pairs with similar amplification efficiency may be pooled in separate multiplex PCR reactions to have better representation of all targets. These PCR reactions may be combined after amplification.

In other embodiments, PCR amplification may be performed at a uniform temperature (isothermal PCR). Examples of isothermal PCR methods may include the ramification amplifying method and the helicase-dependent amplification method. In a preferred embodiment of the invention, PCR amplification may be by thermal cycling between a high temperature to melt the nucleic acid strands, a lower temperature to anneal the primers to the target nucleic acid, and an intermediate temperature compatible with the nucleic acid polymerase to elongate the nucleic acid sequence. In one embodiment, the melting temperatures may be about 85, 86, 87, 88, 89, 90, 95, or 100 degrees Celsius. In a preferred embodiment, the melting temperature may be about 90, 91, 92, 93, 94, 95, 96, 97 or 98 degrees Celsius. In another embodiment, the annealing temperatures may be 30, 35, 40, 45, 50, 55, 60, 65, 70, 75 degrees Celsius or more. In a preferred embodiment, the annealing temperature may be 51, 52, 53, 54, 55, 56, 57, 58, 59, 60, 61, 62, 63, 64, 65, 66, 67, 68, 69, 70, 71, or 72 degrees Celsius. In yet another embodiment, the elongation temperature may be 30, 35, 40, 45, 50, 55, 60, 65, 70, 75, 80 degrees Celsius or more. In a preferred embodiment, the elongation temperature may be 70, 71, 72, 73, 74, 75, 80 degrees Celsius or more.

In certain embodiments, the PCR reaction may be incubated at the melting temperature for about 5 to about 60 seconds. In a preferred embodiment, the PCR reaction may be incubated at the melting temperature for about 30 seconds. In some embodiments, the PCR reaction may be incubated at the annealing temperature for about 5 to about 60 seconds. In a preferred embodiment, the PCR reaction may be incubated at the annealing temperature for about 30 seconds. In some embodiments, the PCR reaction may be incubated at the elongation temperature for about 1 to about 10 minutes. In a preferred embodiment, the PCR reaction may be incubated at the elongation temperature for about 6 minutes. In some embodiments, the PCR reaction is pre-incubated at the melting temperature for about 1, 2, 3, 4, 5, 6, 7, 8, 9 or 10 minutes before cycling between the melting, annealing and elongation temperatures. In a preferred embodiment, the PCR reaction may be pre-incubated at the melting temperature for about 2 minutes.

In several embodiments, the PCR reactions may be cycled between the melting, annealing and elongation temperatures 2, 5, 10, 15, 20, 25, 30, 35, 40, 45, 50, 55 or more times. In a preferred embodiment, the PCR reactions may be cycled between the melting, annealing and elongation temperatures 2, 3, 4, 5, 6, 7, 8, 9, 10, 11, 12, 13, 14, 15 or more times.

D) Trimming Applications

It is contemplated in some embodiments of the process, methods and systems disclosed herein, that the single-stranded DNA on the outer flanks of the patch oligonucleotides may be trimmed, leaving the reduced targeted region defined by the double-stranded DNA created when the oligonucleotides bind to the targeted region. This, for example, occurs in one step of the disclosed PDP process. In preferred embodiments, the unincorporated single-stranded DNA on the outer flanks of the patch oligonucleotides may be removed using enzymes such as exonucleases, enzymes that cleave nucleotides from the end of a polynucleotide sequence. In general, the reduced targeted regions in this process are protected from degradation because they are flanked by double-stranded Patch-bound DNA. Enzymes may also be utilized in the process, method and systems disclosed herein to remove all of the unprotected primers and non-targeted DNA after the universal primers are ligated to the ends of the reduced targeted region.

E) Patches Oligonucleotides

In general, patch oligonucleotides, as that term is used herein, are a string of oligonucleotides of variable length that contain, at a minimum, a sequence that is the reverse complement to the sequence that defines a targeted region. Generally, in the process, methods and systems disclosed herein, annealing of the restriction enzyme-directing oligonucleotides to the nucleic acid templates may be performed by melting the nucleic acid strands at a high temperature, followed by a lower temperature suitable for annealing the restriction enzyme-directing oligonucleotides to target nucleic acid sequences. In one embodiment, the melting temperatures may be about 85, 86, 87, 88, 89, 90, 95, or 100 degrees Celsius. In a preferred embodiment, the melting temperature may be about 90, 91, 92, 93, 94, 95, 96, 97 or 98 degrees Celsius. In another embodiment, the annealing temperatures may be about 10, 15, 20, 25, 30, 35, 40, 45, 50, 55 degrees Celsius or more. In a preferred embodiment, the annealing temperatures may be about 25, 26, 27, 28, 29, 30, 31, 32, 33, 34, 35, 36, 37, 38, 39, 40, 41, 42, 43, 44, 45, 46, 47, 48, 49, 50, 51, or 52 degrees Celsius.

In other embodiments, the annealing reactions may be incubated at the melting temperature for about 5 to about 30 minutes. In a preferred embodiment, the annealing reactions may be incubated at the melting temperature for about 10, 11, 12, 13, 14, 15, 16, 17, 18, 19, 20, 21, 22, 23, 24, 25 minutes. In some embodiments, the annealing reactions may be incubated at the annealing temperature for about 1 to about 10 minutes. In a preferred embodiment, the annealing reactions may be incubated at the melting temperature for about 1, 2, 3, 13, 4, 5, 6, 7, 8, 9, 10, 11, 12, 13, 14, or 15 minutes.

F) Single Strand Specific Exonuclease Degradation

In the processes, methods and systems disclosed herein, single strand specific exonuclease enzyme digestion of nucleic acid templates protected by locus-specific oligonucleotides patches may be used to define ends of the targeted region. This is facilitated by upstream and downstream oligonucleotide patches that anneal to the targeted region and serve as protection against digestion by the single strand specific exonuclease enzymes. Thus, components of the exonuclease reaction may include the nucleic acid sequence to be digested, one or more single strand specific exonuclease enzymes, the oligonucleotide patches protecting the nucleic acid targeted region, and salts and buffers essential for optimal activity of the exonucleases in the reaction.

Non-limiting examples of single strand specific exonuclease enzymes suitable for the methods of the invention may be exonuclease VII, exonuclease I, RecJ exonuclease, or Terminator™ 5'-Phosphate-Dependent Exonuclease (Epicentre Biotechnologies). The upstream and downstream oligonucleotide patches may be designed using primer length, GC pair content, and melting temperature criteria.

Annealing of the protecting oligonucleotides patches to the nucleic acid targeted regions may generally be performed before addition of the exonuclease enzymes. In addition to the fgDNA, annealing reactions may generally contain about 1 µM to about 500 nM of each oligonucleotide. In some embodiments, annealing of the oligonucleotides may be performed by melting the nucleic acid strands at a high temperature, followed by a lower temperature suitable for annealing the protecting oligonucleotides to target loci. In one embodiment, the melting temperatures may be about 85, 86, 87, 88, 89, 90, 95, or 100 degrees Celsius. In a preferred embodiment, the melting temperature may be about 90, 91, 92, 93, 94, 95, 96, 97 or 98 degrees Celsius. In another embodiment, the annealing temperatures may be about 10, 15, 20, 25, 30, 35, 40, 45, 50, 55 degrees Celsius or more. In a preferred embodiment, the annealing temperatures may be about 25, 26, 27, 28, 29, 30, 31, 32, 33, 34, 35, 36, 37, 38, 39, 40, 41, 42, 43, 44, 45, 46, 47, 48, 49, 50, 51, or 52 degrees Celsius.

In some embodiments, the annealing reactions may be incubated at the melting temperature for about 5 to about 30 minutes. In a preferred embodiment, the annealing reactions may be incubated at the melting temperature for about 10, 11, 12, 13, 14, 15, 16, 17, 18, 19, 20, 21, 22, 23, 24, 25 minutes. In some embodiments, the annealing reactions may be incubated at the annealing temperature for about 1 to about 10 minutes. In a preferred embodiment, the annealing reactions may be incubated at the melting temperature for about 1, 2, 3, 13, 4, 5, 6, 7, 8, 9, 10, 11, 12, 13, 14, or 15 minutes. After annealing of the protecting oligonucleotides, the exonuclease enzymes may be added for digestion.

G) Ligation of Universal Primer Sequences

One aspect of the PDP and PtG methods disclosed herein is the ligation of universal primer sequences to nucleic acid sequences. In general, this is facilitated by upstream and downstream nucleic acid patch oligonucleotides that anneal upstream and downstream of the target nucleic acid sequences and serve as a patch between the desired sequence and upstream and downstream universal primers to be ligated. Thus, nucleic acid patch ligation reactions generally contain the target sequences, the upstream and downstream universal primers to be ligated, the upstream and downstream nucleic acid patch oligonucleotides to guide the specific ligation of the universal primers, and the enzymes and other components needed for the ligation reaction.

1. Universal Primers

The upstream and downstream universal primers may be designed using primer length, GC pair content and melting temperature criteria. In some embodiments, the downstream universal primer may be modified to facilitate further steps of the invention. In a specific embodiment, the downstream universal primer may be modified with a 5' phosphate group to enable ligation of the downstream universal primer to the amplicon. In other specific embodiments, the 3' end of the downstream universal primer may be modified for protection against exonuclease digestion. Modifications at the 3' end may be introduced at the time of synthesis or after synthesis through chemical means well known to those of skill in the art. Modifications may be 3' terminal or slightly internal to the 3' end. Some examples of modifications that make nucleic acid sequences exonuclease resistant include, but are not limited to, locked nucleic acids (LNA's), 3'-linked amino groups, 3' phosphorylation, the use of a 3'-terminal cap (e.g., 3'-aminopropyl modification or by using a 3'-3' terminal linkage), phosphorothioate modifications, the use of attachment chemistry or linker modification such as Digoxigenin NHS Ester, Cholesteryl-TEG, biotinylation, thiol modifications, or addition of various fluorescent dyes and spacers such as C3 spacer. In a preferred embodiment, the downstream universal primer is protected from exonuclease digestion by a C3 spacer.

2. Nucleic Acid Patch Primers

In some embodiments, an upstream and a downstream nucleic acid patch oligonucleotide may be designed for each targeted region of fgDNA. In some preferred embodiments, the 5' ends of the upstream nucleic acid patch oligonucleotides may be complementary to sequences in the fgDNA and may be concatenated to upstream nucleotide sequences complementary to the upstream universal primer sequence on the 3' end. In other preferred embodiments, the 3' ends of the downstream nucleic acid patch oligonucleotides may be complementary to downstream sequences in the fgDNA, and may be concatenated to nucleotide sequences complementary to the downstream universal primer sequence on the 5' end.

3. Ligation of Universal Primers

In some embodiments, the universal primers may be ligated to nucleic acid sequences. In a process similar to a PCR amplification reaction, multiple cycles of heating and cooling may be used to melt the target nucleic acid sequence, anneal the nucleic acid patch and universal primers, and ligate the universal primers to target nucleic acid sequences.

In some embodiments of the invention, the universal primers of the invention may be ligated to the target nucleic acids using a DNA ligase. The ligase may be thermostable. In preferred embodiments, the ligase is a thermostable DNA ligase. A thermostable DNA ligase is an enzyme that is relatively stable to heat and eliminates the need to add enzyme prior to each ligation cycle. Non-limiting examples of thermostable DNA ligases may include Ampligase® Thermostable DNA Ligase, Taq DNA Ligase from *Thermus aquaticus*, Tfi DNA ligase from *Thermus filiformis*, Tth DNA ligase from *Thermus thermophilus*, Thermo DNA ligase, Pfu DNA ligase from *Pyrococcus furiosus*, and thermostable DNA ligase from *Aquifex pyrophilus*. The thermostable polymerase may be used in its wild type form, modified to contain a fragment of the enzyme, or to contain a mutation that provides beneficial properties to facilitate the ligation reaction. In a preferred embodiment, the thermostable ligase is Ampligase®.

4. Ligation Reaction Conditions

Ligation reactions may generally contain about 1 µM to about 500 nM of each nucleic acid patch oligo, about 1 µM to about 500 nM of each universal primer, about 3, 4, 5, 6, 7, or 8 units of Ampligase®, and 1 times Ampligase Reaction Buffer.

In some embodiments, ligation reactions may be performed by thermal cycling between a high temperature to melt the nucleic acid strands, a sequence of 1, 2, 3, 4 or 5 lower temperatures to anneal the nucleic acid patch oligonucleotides to the target nucleic acid, and a temperature compatible with the ligase to ligate the nucleic acid sequence. In a preferred embodiment, ligation reactions may be performed by thermal cycling between a high temperature to melt the nucleic acid strands, a first lower temperature to anneal the nucleic acid patch oligonucleotides to the target nucleic acid, a second lower temperature to anneal the universal primers to the nucleic acid patch oligonucleotides, and a temperature compatible with the ligase to ligate the nucleic acid sequence. In one embodiment, the melting temperatures may be about 85, 86, 87, 88, 89, 90, 95, or 100 degrees Celsius. In a preferred embodiment, the melting temperature may be about 90, 91, 92, 93, 94, 95, 96, 97 or 98 degrees Celsius. In another embodiment, the Nucleic acid patch oligonucleotide annealing temperatures may be about 30, 35, 40, 45, 50, 55, 60, 65, 70, 75 degrees Celsius or more. In a preferred embodiment, the nucleic acid patch oligonucleotide annealing temperatures may be about 45, 46, 47, 48, 49, 50, 51, 52, 53, 54, 55, 56, 57, 58, 59, 60, 61, 62, 63, 64, 65, 66, 67, 68, 69, 70, 71, or 72 degrees Celsius. In another embodiment, the ligation temperature may be about 30, 35, 40, 45, 50, 55, 60, 65, 70, 75, 80 degrees Celsius or more. In a preferred embodiment, the ligation temperature may be about 55, 56, 57, 58, 59, 60, 61, 62, 63, 64, 65, 66, 67, 68, 69, 70 degrees Celsius or more.

In some embodiments, the ligation reactions may be incubated at the melting temperature for about 5 to about 60 seconds. In a preferred embodiment, the ligation reactions may be incubated at the melting temperature for about 30 seconds. In some embodiments, the ligation reactions may be incubated at the nucleic acid patch oligonucleotide annealing temperature for about 1, 2, 3, 4, 5, 6, 7, 8, 9, 10 or more minutes. In a preferred embodiment, the reactions may be incubated at the nucleic acid patch oligonucleotide annealing temperature for about 2 minutes. In some embodiments, the ligation reactions may be incubated at the universal primer annealing temperature for about 30 seconds to about 5 minutes. In a preferred embodiment, the ligation reactions may be incubated at the universal primer annealing temperature for about 1 minute. In some embodiments, the ligation reactions may be incubated at the ligation temperature for about 30 seconds to about 5 minutes. In a preferred embodiment, the ligation reactions may be incubated at the ligation temperature for about 1 minute. In some embodiments, the reactions may be pre-incubated at the melting temperature for about 5, 6, 7, 8, 9, 10, 15, 20 or 25 minutes before cycling between the melting, annealing and ligation temperatures. In a preferred embodiment, the ligation reactions may be pre-incubated at the melting temperature for about 15 minutes.

In some embodiments, the ligation reactions may be cycled between the melting, annealing and ligation temperatures about 10, 50, 100, 150, 200 or more times. In a preferred embodiment, the ligation reactions may be cycled between the melting, annealing and elongation temperatures about 100 times.

H) Degrade Mispriming Products and Genomic DNA

In some embodiments of the PDP and PtG methods and processes herein disclosed, exonucleases may be added to the ligation reaction at the completion of the reaction to degrade mispriming products of the multiplex PCR reaction or genomic DNA. In preferred embodiments, exonucleases may be 3' to 5' exonucleases. Exonucleases may be single stranded or double stranded exonucleases. Non-limiting examples of exonucleases suitable for this step of the reaction may include exonuclease I, exonuclease III and mung bean nuclease. One or more exonucleases may be added. In a preferred embodiment, the exonucleases may be exonuclease I and III.

I) Sample-Specific Barcode PCR and Sequencing of Resultant Nucleic Acid Patch Amplicons In some aspects of the invention, nucleic acid samples may be sequenced. In some embodiments, the nucleic acids sequenced may be the amplicons prepared in PDP and PtG described above. Sequencing techniques suitable for the invention may be high throughput. High throughput sequencing techniques may include techniques based on chain termination, pyrosequencing (sequence by synthesis), or sequencing by ligation and are well known to those of skill in the art. In some embodiments, high throughput sequencing techniques like true single molecule sequencing (tSMS) may not require amplification of target nucleotide sequences. In preferred embodiments, sequencing may be performed using high throughput sequencing techniques that involve in vitro clonal amplification of the target nucleotide sequence. Non-limiting examples of high throughput sequencing techniques that involve amplification may include solid-phase PCR in polyacrylamide gels, emulsion PCR, rolling-circle amplification, bridge PCR, BEAMing (beads, emulsions, amplification and magnetics)-based cloning on beads, massively parallel signature sequencing (MPSS) to generate clonal bead arrays. In a preferred embodiment, the amplicons may be sequenced using PCR techniques as exemplified by 454 Sequencing TM.

In some embodiments, the PCR may use primers complementary to the universal primer sequences. In other embodiments, the PCR primers may be coupled to nucleic acid sequences for sequencing. In a preferred embodiment, the primers for the final universal PCR may be tailed to 454 sequencing primers A and B (454 Life Sciences, Branford, Conn.). In other embodiments, the primers for the PCR amplification may be complementary to upstream and downstream universal primer nucleotide sequences. In additional embodiments, the PCR primers may be coupled to nucleic acid sequence barcodes. In some embodiments, the nucleic acid barcode may be about 4, 5, 6, 7, 8, 9, 10, or more bases. In a preferred embodiment, the nucleic acid barcode may be about 6 bases. The barcodes may be at the 5' end, the 3' end or, internal to the primer sequence.

In some embodiments, nucleic acid sequences amplified in the PCR reactions of more than one sample may be pooled for parallel sequencing of nucleic acids prepared in multiple samples. In some embodiments, about 2, 3, 4, 5, 10, 15, 20, 30, 40, 50, 60, 70, 80, 90, 100, 1000 or more samples may be pooled for sequencing.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A method for the capture and amplification of a targeted region of fragmented deoxyribonucleic acid (fgDNA), the method comprising:
   providing a sample of an fgDNA having a targeted region between two unknown sequences;
   reducing said sample of said fgDNA to single stranded fgDNA;
   adding oligonucleotide patches to said single stranded fgDNA, each of said oligonucleotide patches comprising:
      a nucleotide sequence complementary to an end of said targeted region;
      a universal primer sequence; and
      a protecting group on at least one end;
   one of said oligonucleotide patches binding to each of said ends of said targeted region creating double stranded DNA at both said ends of said targeted region and leaving single stranded DNA flanking regions outside said targeted region, said single stranded DNA flanking regions being of unknown length and sequence;
   adding enzymes to said single stranded fgDNA, the enzymes cleaving said single stranded DNA flanking regions from said double stranded DNA at both said ends of said single stranded fgDNA, resulting in said single stranded fgDNA being reduced to targeted region with said double stranded DNA at both said ends said protecting group preventing said oligonucleotide patch from degradation by said enzymes;
   ligating a complementary universal primer to each of said ends of said targeted region;
   performing polymerase chain reaction; and
   sequencing the polymerase chain reaction amplicons of said targeted region.

2. The method of claim 1, wherein a multiplicity of oligonucleotide patch pairs are added to the reaction concurrently.

* * * * *